US00PP37554P2

(12) United States Plant Patent
Heuger

(10) Patent No.: US PP37,554 P2
(45) Date of Patent: Aug. 4, 2026

(54) ***HELLEBORUS* PLANT NAMED 'HL 1052'**

(50) Latin Name: ***Helleborus* x *niger* X Helleborus x *hybridus***
Varietal Denomination: HL 1052

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,951

(22) Filed: Nov. 23, 2025

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HL 1052', characterized by its upright to outwardly spreading and mounded plant habit; moderately vigorous growth habit; dark green-colored leaflets; freely flowering habit; flowers with purplish red-colored sepals with narrow white-colored marginal edges; and good garden performance.

2 Drawing Sheets

Figure 1:
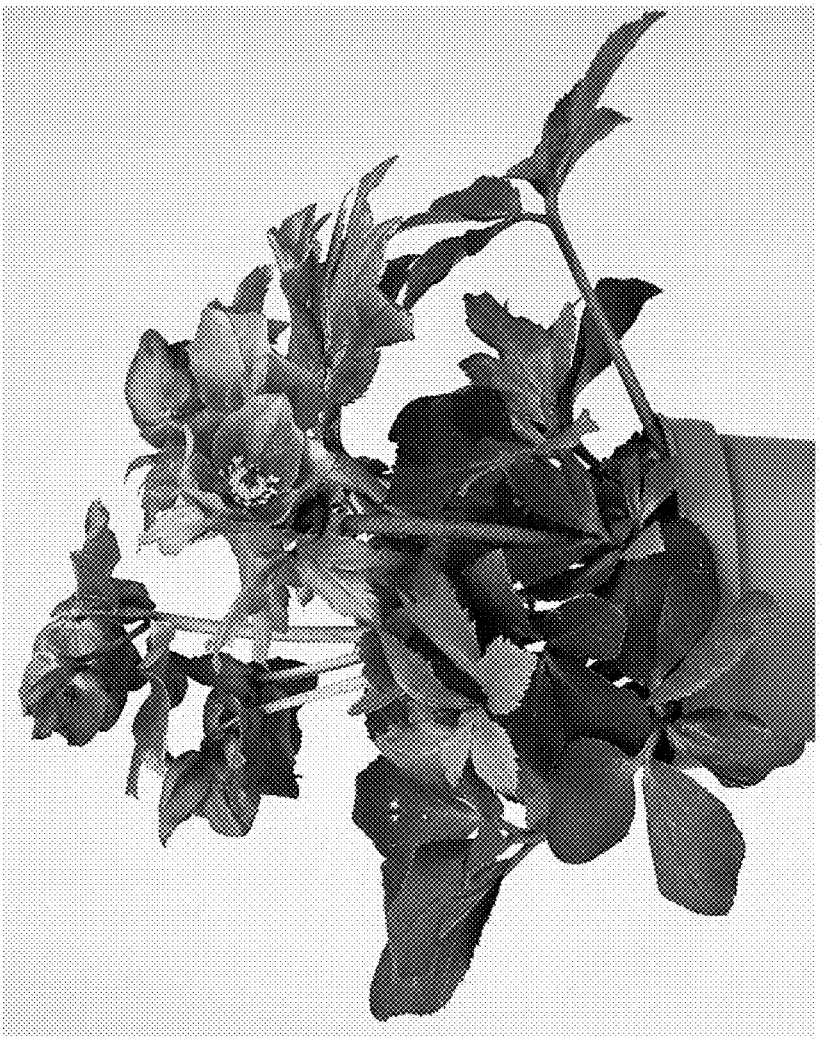

Botanical designation: *Helleborus* x *niger* X *Helleborus* x *hybridus*.

Cultivar denomination: 'HL 1052'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2901. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/983. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1052'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2016 of a proprietary selection of *Helleborus* x *niger* identified as code number 028, not patented, as the female, or seed, parent and a proprietary selection of *Helleborus* x *hybridus* identified as code number 16-10, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2018.

Asexual reproduction of the new *Helleborus* plant by in vitro axillary meristem culture in a controlled environment in Glandorf, Germany since October, 2019 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1052'. These characteristics in combination distinguish 'HL 1052' as a new and distinct *Helleborus* plant:

1. Upright to outwardly spreading and mounded plant habit.
2. Moderately vigorous growth habit.
3. Dark green-colored leaflets.
4. Freely flowering habit.
5. Flowers with purplish red-colored sepals with narrow white-colored marginal edges.
6. Good garden performance.

Plants of the new *Helleborus* differ from plants of the female parent selection in the following characteristics:

1. Leaflets of plants of the new *Helleborus* are darker green in color than leaflets of plants of the female parent selection.
2. Flower sepals of plants of the new *Helleborus* are purplish red in color red in color with narrow white-colored marginal edges whereas flower sepals of plants of the female parent selection are white in color.

Plants of the new *Helleborus* differ from plants of the male parent selection in the following characteristics:

1. Leaflets of plants of the new *Helleborus* are lighter green in color than leaflets of plants of the male parent selection.
2. Flower sepals of plants of the new *Helleborus* are purplish red in color red in color with narrow white-colored marginal edges whereas flower sepals of plants of the male parent selection are red in color.

Plants of the new *Helleborus* can also be compared to plants of *Helleborus* x *niger* X *Helleborus* x *hybridus* 'HL 1010', disclosed in U.S. Plant Pat. No. 34,932. In side-by-side comparisons, plants of the new *Helleborus* differ primarily from plants of 'HL 1010' in the following characteristics:

1. Leaflets of plants of the new *Helleborus* are lighter green in color than leaflets of plants of 'HL 1010'.
2. Flower sepals of plants of the new *Helleborus* are purplish red in color red in color with narrow white-colored marginal edges whereas flower sepals of plants of 'HL 1010' are solid purplish red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1052' grown in a container.

Figure 2:
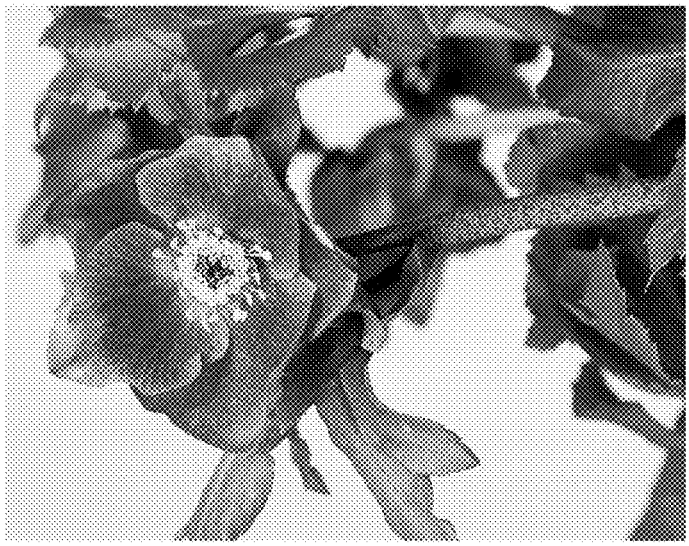

The photograph at the left of the second sheet (FIG. 2) is a close-up view of a typical flower of 'HL 1052'.

Figure 3:
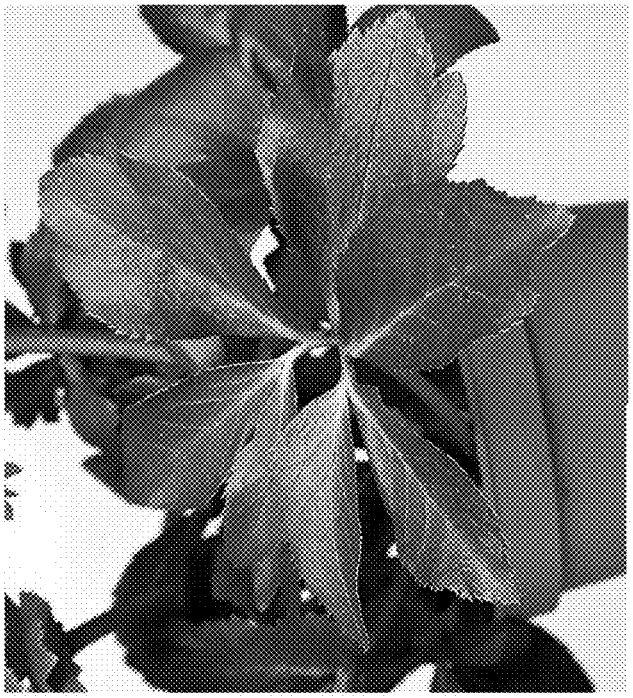

The photograph at the right of the second sheet (FIG. 3) is a close-up view of typical leaflets of 'HL 1052'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1052'.

Parentage:

*Female, or seed, parent*.—Proprietary selection of *Helleborus* x *niger* identified as code number 028, not patented.

*Male, or pollen, parent*.—Proprietary selection of *Helleborus* x *hybridus* identified as code number 16-10, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous growth habit and moderate growth rate.

*Plant height, soil level to top of foliar plane*.—About 20.7 cm.

*Plant height, soil level to top of flowers*.—About 24.7 cm.

*Plant diameter* (*area of spread*).—About 40.7 cm.

Leaf description:

*Arrangement*.—Leaves arranged in a basal rosette; leaves palmately compound with typically five leaflets per leaf.

*Leaf length*.—About 17.1 cm.

*Leaf width*.—About 18.9 cm.

*Leaflet length*.—About 10.4 cm.

*Leaflet width*.—About 5.6 cm.

*Leaf shape*.—Palmate; roughly reniform in outline.

*Leaflet shape*.—Broadly elliptic to elliptic-obovate; lowest leaflets are typically cleft.

*Leaflet apex*.—Acute.

*Leaflet base*.—Attenuate.

*Leaflet margin*.—Serrate; coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; slightly glossy.

*Leaflet venation pattern*.—Pinnate and reticulate.

*Leaflet color*.—Developing leaflets, upper surface: Close to 138A; at the base, close to 187A. Developing leaflets, lower surface: Close to 138B; main veins, close to 187B. Fully developed leaflets, upper surface: Close to 147A; at the base, tinged with close to N187A; venation, close to 144C. Fully developed leaflets, lower surface: Close to 147B; venation, close to 144C.

*Petioles*.—Length: About 14.5 cm. Diameter: About 6 mm by 6.5 mm. Strength: Strong. Texture and luster, upper and lower surfaces: Smooth, glabrous; slightly glossy. Color, upper surface: Close to 144A with dots, close to N186C. Color, lower surface: Close to 144B with dots, close to 177A.

Flower description:

*Flower shape and habit*.—Single rotate bowl-shaped flowers arranged in panicles; freely flowering habit with about three flowers per inflorescence and about 20 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.5 cm. Diameter: About 1.6 cm. Shape: Ovate to oblong. Texture and luster: Smooth, glabrous; slightly glossy. Color: Close to 186A; towards the base, strongly tinged with close to 145C.

*Inflorescence height* (*including peduncle*).—About 27.9 cm.

*Inflorescence diameter*.—About 13.1 cm.

*Flower diameter*.—About 5.5 cm.

*Flower depth*.—About 4 cm.

*Petals*.—All petals are transformed into nectaries.

*Sepals*.—Quantity and arrangement: About five, arranged in a single whorl. Length: About 5.1 cm. Width: About 4.4 cm. Shape: Broadly ovate; moderately concave. Apex: Obtuse. Base: Cuneate. Margin: Entire; slightly undulate. Texture and luster, upper and lower surfaces: Smooth, glabrous; matte. Color: When opening, upper surface: Close to a blend of N186D and 187D; distal margins, close to 69B; at the apex, close to N77B; at the base, close to 144C. When opening, lower surface: Close to 71D; distal margins, close to 63D; at the apex, close to 71D; venation, close to 187D. Fully opened, upper surface: Close to a blend of 72C and 186C; narrow marginal edges, close to NN155D; at the apex, tinged with close to 138B; at the base, close to a blend of 138B and 138C. Fully opened, lower surface: Close to N186D; occasional narrow marginal edges, close to NN155D; at the apex, tinged with close to 145C; venation, close to 187B. Flower bracts: Quantity per flower: Typically one or two. Length: About 5.9 cm. Width: About 3.9 cm. Shape: Ovate, occasionally with one to two shallow lobes. Apex: Acute to tri-lobed. Base: Truncate to cuneate. Margin: Entire and distally, serrate; coarsely undulate. Color, upper surface: Close to NN137B. Color, lower surface: Close to 147B and 147C.

*Peduncles*.—Length: About 23.1 cm. Diameter: About 7.5 mm to 8.3 mm. Aspect: About 10° from vertical. Strength: Strong. Texture and luster: Smooth, glabrous; moderately glossy. Color: Close to 144D; heavily covered with fine dots, close to a blend of 183A and 187C.

*Pedicels*.—Length: About 2 cm. Diameter: About 4 mm. Aspect: About 22.5° from peduncle axis. Strength: Moderately strong. Texture and luster: Smooth, glabrous; slightly to moderately glossy. Color: Close to a blend of N77A and N186C; occasionally with dots, close to N144C.

*Reproductive organs*.—Stamens: Quantity per flower: About 100. Filament length: About 1.9 cm. Filament color: Close to 76C. Anther shape: Double and broadly reniform; basifixed. Anther size: About 2 mm by 3 mm. Anther color: Close to 5C. Pollen amount: Sparse. Pollen color: Close to 4D. Pistils: Quantity per flower: About six to eight. Pistil length: About 1.2 cm. Stigma diameter: About 0.3 mm. Stigma shape: Club-shaped. Stigma color: Close to 157D. Style length: About 1.15 cm. Style color: Close to 186A; at the apex, close to 187A. Ovary color: Close to a blend of 145B and 145C. Nectaries (transformed petals): Quantity per flower: About 17 to 21. Length: About 1.2 cm. Diameter: About 5 mm. Shape: Tubular, flattened; apices, obtuse. Texture and luster, inner and outer surfaces: Smooth, glabrous; slightly glossy. Color, immature, inner and outer surfaces: Close to 144C. Color, mature, inner and outer surfaces: Close to 144B; distally, close to 151D; with subsequent development, color becoming closer to 153D and towards the base, close to N144A. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1052' as herein illustrated and described.

* * * * *